May 9, 1967 J. C. MONTGOMERY ETAL Plant Pat. 2,738
ARTICHOKE PLANT
Filed Jan. 3, 1966
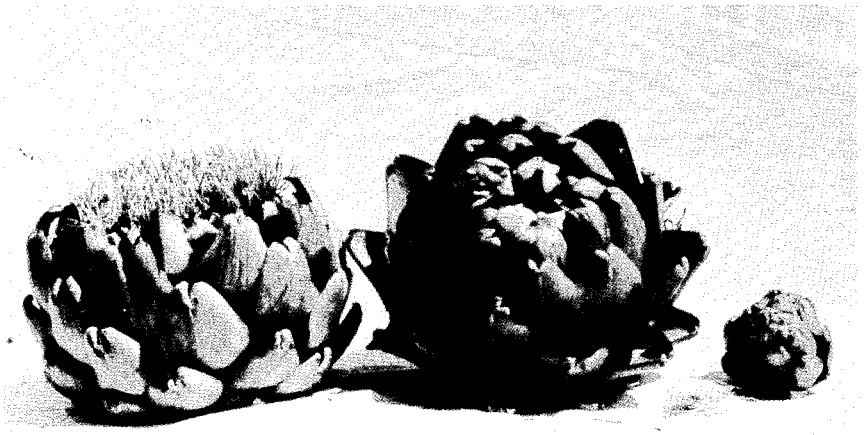
Inventors
Johnson C. Montgomery
James D. Bird United States Patent Office Plant Pat. 2,738
Patented May 9, 1967

2,738
ARTICHOKE PLANT

Johnson C. Montgomery, 3660 Altamont Way, and James D. Bird, 3661 Altamont Way, both of Redwood City, Calif. 94062

Filed Jan. 3, 1966, Ser. No. 519,812
1 Claim. (Cl. Plt.—89)

Our invention relates to a new and distinct variety, in the form of a cultivated sport, of artichoke plant, discovered by Johnson C. Montgomery in 1964 at Redwood City, Calif., and propagated asexually by cutting by James Douglas Bird in 1964 and 1965 at Redwood City, Calif., said artichoke plant having been found in a state of cultivation and having as its parentage the common artichoke (*Cynara scolymus* L.) as extensively cultivated commercially and in private gardens throughout the coastal areas of central California.

The distinctive characteristic of the new variety is the complete absence of sharp bristles on the receptacle and the complete absence of hard, sharp spines on the tips of the phyllaries.

The new variety resulted from somatic mutation and its characteristics are carried through by means of asexual propagation to all plants cut from the original stock.

No plants of the new variety have been sold and the new variety is not found in an uncultivated state. Asexual reproduction can be carried out on a commercial scale.

The new variety has substantially the same growth requirements and growth habits as the common artichoke. It is sometimes larger as a plant; edible buds, in a mature form 10 to 15 percent larger than the common variety; growing season and productivity of buds, substantially identical; disease resistance, insect resistance and frost resistance, substantially identical.

The flavor of the edible portions of the bud of the new variety may be substantially identical to the flavor of the bud of the common artichoke; however, because there is up to two and one half times as much spineless and bristleless edible material in the bud of the new variety as there is in a bud of corresponding size of the common artichoke, much larger bites can be taken of the new variety, the new variety can be eaten entirely without fear and apprehension of prickles in the mouth (as is not the case with the common artichoke) and therefore, to most people who eat the bud of the new variety, the flavor seems greatly superior to the flavor of the common commercial artichoke. The striking characteristic of the new variety is the complete lack of spiny processes which makes it possible to eat the entire bud, excepting only the hardened portions of the very outside leaves. In eating the bud of the new variety, unlike eating the bud of the common variety, it is not necessary to discard the top (spiny in the common artichoke) portions of the inner phyllaries, nor is it necessary to scrape setae from the receptacle.

The following is a detailed description of the new variety, observations having been made on plants which are growing in Redwood City, Calif.

Plant: To 2.0 meters high, with thick, striate, grayish to green, tomentulose stems.

Growth: Robust.

Leaves: Basal leaves in a loose rosette, up to 1.2 meters long, 0.2 to 0.32 meter broad, arachnoid-tomentulose, grayish beneath, glabrate and grayish-green to bright green above, bipinnately divided, the rachis decurrent; cauline leaves sessile, becoming gradually reduced to linear-oblong bracts.

Capitulum prior to anthesis ("bud"): 10.0 to 14.0 centimeters long, two thirds as long as wide, solitary on cymosely clustered branches; involucre broadly ovoid to globose; the phyllaries imbricate and appressed; outside phyllaries, broadly ovate, glabrous, stiffly coriaceous, very fleshy at the base; interior phyllaries, glabrous, not coriaceous, fleshy at the base, blunt and aspinose; receptacle, setose, fleshy, soft, about one third to one half as deep as it is broad.

Flowers: Purplish-blue, achenes 5.0 to 6.0 millimeters long, oblongoid, brown to black; pappus, 2.0 to 3.0 centimeters long, yellowish-white.

Season: Perennial with die-back during November to December.

*Buds.*—May to October (depending in part on the season).

*Flowers.*—September to November (depending in part on the season).

Disease and insect resistance: Seldom touched by any diseases or harmful insects.

Rain and drought resistance: Fair to good, apparently somewhat better than that of the common commercial artichoke.

Use: Market buds for human consumption.

Bearing qualities: Outstanding.

Quality: Outstanding.

The primary characteristics referred to have been found to be fixed in the asexual reproduction of the plant.

We claim:

A new and distinct variety, in the form of a cultivated sport, of artichoke plant, substantially as herein-disclosed, characterized as to novelty by its lack of spines on the tips of the phyllaries; by its high proportion of edible bud material; and by its robust growth and outstanding bearing qualities.

No references cited.

ABRAHAM G. STONE, *Primary Examiner.*

ROBERT E. BAGWILL, *Examiner.*